United States Patent
Goldemann et al.

(10) Patent No.: US 6,752,147 B1
(45) Date of Patent: Jun. 22, 2004

(54) INHALATION APPARATUS FOR POWDER MEDICATIONS

(75) Inventors: Raul Goldemann, Berlin (DE); Detlef Schwarzwald, Berlin (DE)

(73) Assignee: Hagepharm GmbH, Mainz-Finthen (DE)

( * ) Notice: Subject to any disclaimer, the term of this patent is extended or adjusted under 35 U.S.C. 154(b) by 0 days.

(21) Appl. No.: 09/601,170

(22) PCT Filed: Dec. 22, 1998

(86) PCT No.: PCT/DE98/03808

§ 371 (c)(1),
(2), (4) Date: Dec. 11, 2000

(87) PCT Pub. No.: WO99/38555

PCT Pub. Date: Aug. 5, 1999

(30) Foreign Application Priority Data

Jan. 30, 1998 (DE) .......................... 198 04 888
May 29, 1998 (DE) .......................... 198 25 434

(51) Int. Cl.[7] ............................................. A61M 15/00
(52) U.S. Cl. ............................. 128/203.15; 128/203.12
(58) Field of Search ................... 128/200.11, 200.12, 128/200.17, 200.21, 200.22, 200.23, 200.24, 203.12, 203.15, 203.19, 203.21, 203.23, 203.28, 204.12; 604/58, 63

(56) References Cited

U.S. PATENT DOCUMENTS

| | | | | |
|---|---|---|---|---|
| 3,921,637 A | * | 11/1975 | Bennie et al. | 128/203.15 |
| 5,033,463 A | * | 7/1991 | Cocozza | 128/203.21 |
| 5,161,524 A | * | 11/1992 | Evans | 128/203.15 |
| 5,239,992 A | * | 8/1993 | Bougamont et al. | 128/203.15 |
| 5,320,714 A | * | 6/1994 | Brendel | 128/203.15 |
| 5,447,151 A | * | 9/1995 | Bruna et al. | 128/203.15 |
| 5,505,196 A | * | 4/1996 | Herold et al. | 128/203.15 |
| 5,524,613 A | * | 6/1996 | Haber et al. | 128/203.15 |
| 5,568,884 A | * | 10/1996 | Bruna | 222/189.09 |
| 5,575,280 A | * | 11/1996 | Gupte et al. | 128/203.15 |
| 5,702,362 A | * | 12/1997 | Herold et al. | 604/58 |
| 5,797,390 A | * | 8/1998 | McSoley | 128/200.23 |
| 5,975,076 A | * | 11/1999 | Yianneskis et al. | 128/203.15 |
| 6,029,661 A | * | 2/2000 | Whaley et al. | 128/203.15 |
| 6,029,662 A | * | 2/2000 | Marcon | 128/203.15 |
| 6,119,688 A | * | 9/2000 | Whaley et al. | 128/203.15 |
| 6,553,987 B1 | * | 4/2003 | Davies | 128/200.14 |
| 2003/0116157 A1 | * | 6/2003 | Braithwaite et al. | 128/203.15 |

FOREIGN PATENT DOCUMENTS

| | | |
|---|---|---|
| EP | 0549605 | 7/1993 |
| EP | 0559663 B1 | 9/1993 |
| WO | 9205823 | 4/1992 |
| WO | 9208509 | 5/1992 |

* cited by examiner

*Primary Examiner*—Aaron J. Lewis
*Assistant Examiner*—Teena Mitchell
(74) *Attorney, Agent, or Firm*—Webb Ziesenheim Logsdon Orkin & Hanson, P.C.

(57) ABSTRACT

An inhalation device for administering powdered forms of medication includes a housing with a rotatable dosing ball associated with an opening of a powdered reservoir located inside the housing. The dosing ball may be operated manually and includes a peripheral dosing cavity for receiving a dose of powder. The dosing ball is connected with a torsion spring and further includes a stop piece. In addition, the dosing ball is associated with a pivotable trip flap that has a movable limit stop. The dosing ball is preloaded by turning the dosing ball until the stop piece comes to rest on the movable limit stop of the trip flap. The dosing ball is then released as normal user breathing triggers a swaying of the trip flap. The stop piece is configured to hit against the bottom of the housing which abruptly blocks acceleration of the dosing ball, which in turn causes the medicine to be catapulted out of the dosing cavity and be widely dispersed in the stream of respiratory air so that the medicine may be inhaled completed and in sync with respiration. Overdosing or release of multiple doses is thus prevented by the inhalation device.

17 Claims, 6 Drawing Sheets

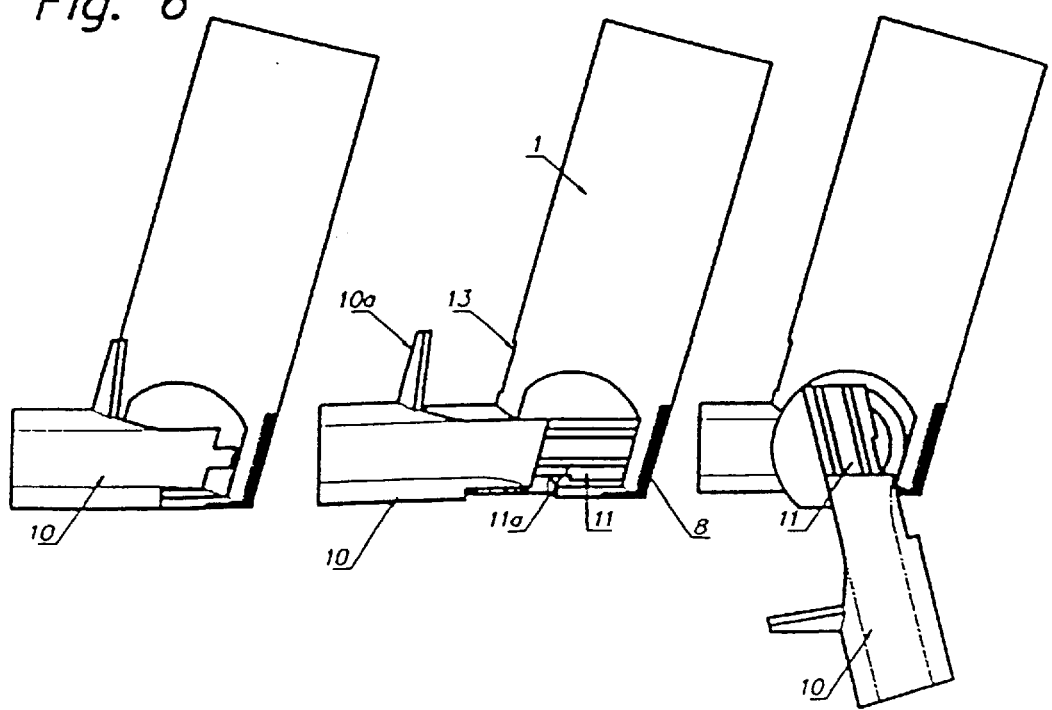

INHALATION APPARATUS FOR POWDER MEDICATIONS

BACKGROUND OF THE INVENTION

Figure 1:
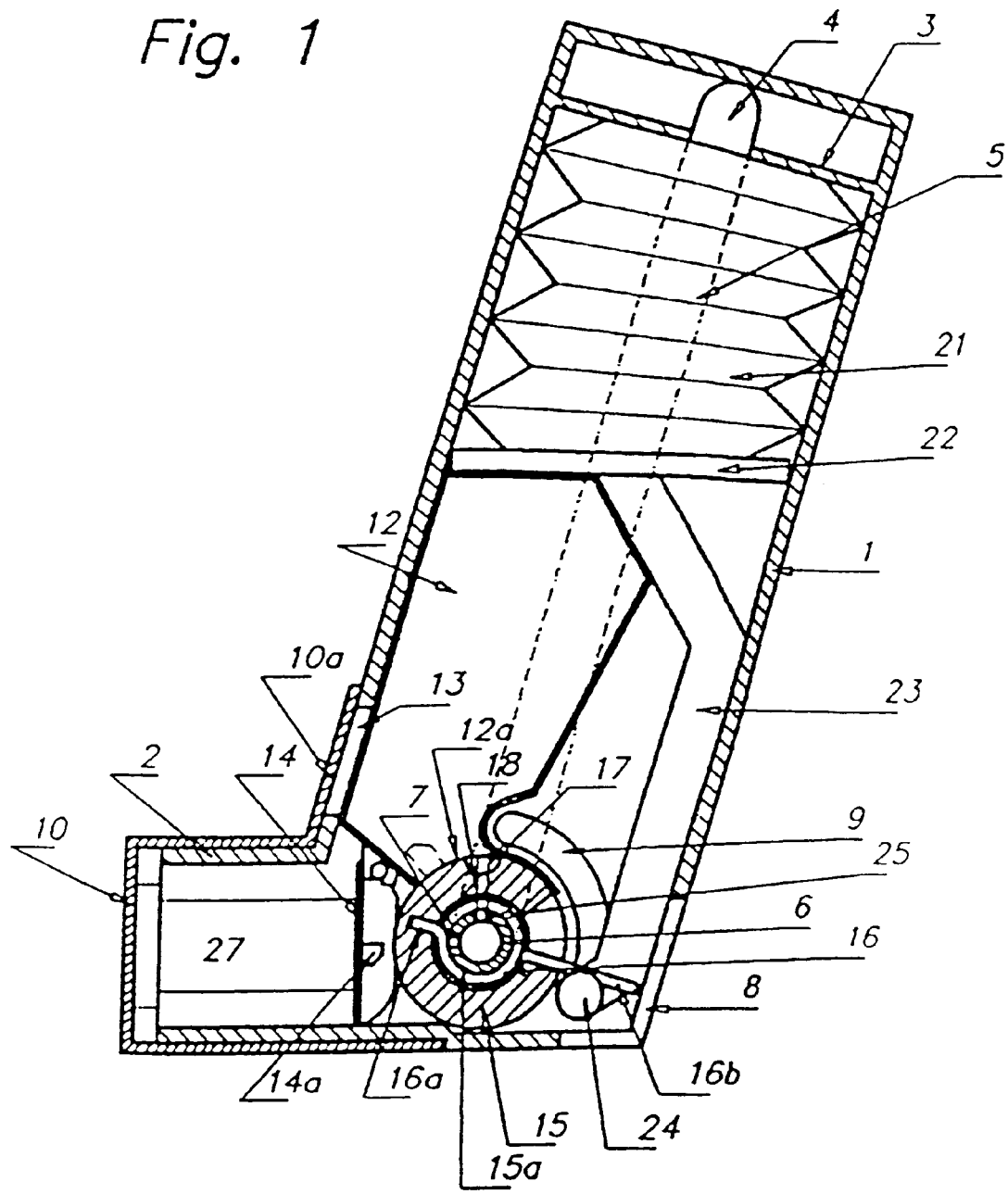

This invention relates to a inhalation device for administering powdered forms of medication which includes a housing with a rotatable dosing apparatus that has a circular perimeter area and is associated with defines opening of a powder reservoir located inside the housing that can be operated manually and comprises a peripheral dosing cavity for receiving a portion of powder, and a mouthpiece connected to the housing at the level of the dosing apparatus and opposing air intake holes so as to form an air duct in which the powder dose released by turning the dosing apparatus is catapulted into the user's stream of respiratory air.

DESCRIPTION OF THE PRIOR ART

An inhalation device of this type that works without a propellant or additional air has been described, for example, in EP 0 559 663. This powder inhalator comprises a reservoir filled with a powdered form of medication that is located inside a housing, the funnel-shaped opening of which being locked by a dosing drum that can be turned manually. The perimeter of the dosing drum comprises at least one dosing cavity whose size matches the powder dose to be inhaled and which is filled with medicine whenever it is in the opening range of the powder reservoir. A mouthpiece is connected at the level of the dosing apparatus, and air intake holes are located at the opposite side of the housing. When the dosing drum is turned, the powdered form of medicine falls into the air duct of the mouthpiece, either by mere gravitational force or boosted by a vibrating mechanism, and is inhaled with the patient's stream of inhaled air. The known problem of this device type, i.e. complete discharge of the medicine from the dosing cavity and the mouthpiece which is critical for reliable dispersing and dosing is to be achieved here by a specific air conduction system that causes puff blowing of the dosing chamber and complete inhalation of the powder dose through a short air path.

However, the inhalation devices of the type described have a disadvantage in that the medicine is not completely blown out or is not adequately dispersed in the air stream to ensure reliable dosing when the stream of inhaled air is weak only. Dosing reliability is furthermore reduced by the fact that medicine will be fed into the mouthpiece even if inhalation is weak or does not take place when the dosing apparatus is operated manually but will completely or partly remain there, so that any subsequent inhalation process will result in overdosing or multiple dosing.

To boost the stream of inhaled air, improve dispersion, and make the intake of the medicine more reliable, powder inhalators have been proposed that are equipped with a pumping device to produce an additional stream of compressed air.

For example, a defined dose of a powdered medicinal substance is placed into the flow channel of a mouthpiece located at the side of a propellant-free inhalation device as described in EP 0 549 6051 using a plunger that can be moved by pressing a button inside a lateral recess forming a dosing cavity. At the same time, one interior wall of said dosing cavity is in communication with the cylinder of a pump. The preloaded plunger of the pump is released using a switching device operated by inhaling to produce an air stream which places the powdered medicinal substance via a nozzle into the stream of inhaled air and spreads it therein.

This inhalation device consists of a multitude of the most various components due to sophisticated mechanisms for dosing and for producing and releasing an additional stream of compressed air. Such inhalators are therefore very expensive as regards manufacture and assembly of their components, and they are susceptible to failure due to their complicated design and the required interaction of various elements, especially when dust, dirt, and breathing moisture can intrude. Moreover, complete- charging of the dosing cavity which forms a lateral recess cannot be guaranteed or can only be ensured by adding more components. As said additional stream of air is produced by the motion of the pump plunger and conducted to the dosing cavity via a sieve bottom, the required blowing pressure to be exerted upon the powdered medicine is either weak or requires a powerful pumping unit.

Another decisive disadvantage of this solution is the fact that the powdered form of medication is in the mouthpiece before the stream of compressed air is released in sync with respiration, and that it remains there if it is not inhaled. On the one hand, this may result in double dosage when the medicine is taken at a later point in time, on the other hand the medicinal substance lying bare can be contaminated or get moist, which would impede the operation of the powder inhalator. In addition, the known powder inhalators are not adequately protected against intrusion of dirt and moisture, especially breathing moisture, or unintentional release of the powdered form of medicine.

It is therefore the problem of this invention to provide an inhalation device of the type described above that has a simple design, allows safe handling, can be produced at low cost, and guarantees exact dosing and complete inhalation of the powdered form of medicine, thereby reliably excluding overdosing and multiple doses.

SUMMARY OF THE INVENTION

The inhalation device of the present invention includes a dosing apparatus is that connected with elastic fastening devices and includes a stop piece, and the dosing apparatus can be preloaded until it hits on a movable limit stop while the dosing cavity remains within the range of the powder dispensing hole of the powder reservoir, the limit stop being movable by the user's breathing air for releasing the preloaded dosing apparatus. The accelerated motion of the dosing apparatus can be blocked suddenly by the stop piece.

In other words, the basic concept of this invention is to preload the dosing apparatus before the medicine is taken or before the dosing cavity containing the medicine is placed within the air duct, and that it is held in said preloaded condition to a limit stop that can be moved by inhaling. Inhaling releases and accelerates the dosing apparatus, and its accelerated motion is stopped abruptly when the stop piece of said dosing apparatus hits on the housing or housing bottom. This sudden interruption of the rotation of the dosing apparatus causes the powdered form of medication to be flung out of the dosing cavity at high speed and to be widely dispersed across the air duct. At the same time, the user's inhalation air which caused the release of the dosing cavity and the medicine is still active so that the finely dispersed powder dose is directly carried over into the stream of the user's respiratory air and completely taken in by the user's body via his or her respiratory tract. As the medicine is released by respiration, it has to be inhaled. Subsequent overdosing or multiple dosing due to residual powder in the mouthpiece from a previous inhalation attempt is therefore excluded.

In accordance with another aspect of the invention said dosing cavity is designed as a dosing ball. The benefit of this design is that the air stream is swirled in the air duct which improves the dispersion of the powder.

In accordance with yet another aspect of the invention, the movable limit stop that keeps the dosing ball in a preloaded condition is attached to a trip flap that shuts the air duct and is pivotably hinged in the air duct. When the user breathes in, a negative pressure is generated that swings the trip flap and limit stop to release the rotation of the preloaded dosing ball. Moreover, said pivotable trip flap prevents the intrusion of moisture into the interior of the housing as may be caused by unintentional exhaling into the mouthpiece An advantageous improvement of the invention comprises an operating lever for turning and preloading the dosing ball that is attached to the external side of the housing and to which a cap for sealing the mouthpiece of the inhalation device is slidably mounted on rails. Thus the cap will always be connected to the device and cannot be lost. Consequently, any risk of contamination or unintentional actuation of the arrested operating lever is either very low or completely excluded.

In accordance with another aspect of the design of the invention, a pumping device is provided in the housing whose reservoir of compressed air is in communication with the dosing cavity via a valve unit in such a way that when the preloaded dosing ball is triggered in sync with inhalation, i. e. when the powder dose is released from the powder reservoir, the valve unit will simultaneously release compressed air to the dosing cavity or to the medicine contained therein. This improves the dispersion of the powdered form of medication, especially in the early phase of deagglomeration. It also guarantees complete and reliable intake of the medicine by users with reduced respiratory capacity such as older people or children.

Other features, useful designs and benefits of the invention follow from the description of an embodiment of the invention below.

BRIEF DESCRIPTION OF THE DRAWING

Two embodiments of the invention shall now be explained in more detail with reference to the attached figures, wherein:

FIG. 1 shows a lateral sectional view of the inhalation device of the invention in its closed initial position, FIG. 2 shows the inhalation device of FIG. 1 with the cap removed from the mouthpiece and folded downwards;

FIG. 3 shows a diagrammatic sectional view of the inhalation device of FIGS. 1 and 2 at the time when the powdered form of medicinal substance is inhaled;

FIG. 4 shows a lateral sectional view of an inhalation device according to the invention working without an additional stream of compressed air in its initial closed position;

FIG. 5 shows an inhalation device with an integrated nasal adapter in its mouthpiece; and FIG. 6 shows three side views of the powder inhalator with different cap positions.

DETAILED DESCRIPTION OF THE PREFERRED EMBODIMENTS

The powder inhalation device that provides an additional stream of compressed air according to FIGS. 1 through 3 includes an oblong housing 1 with a mouthpiece 2 fitted laterally to its lower end and a transverse wall 3 at its upper end, the latter comprising an air exit hole 4 in communication with a compressed air duct 5 leading to the lower part of the housing along the inner wall of said housing. The lower part of housing 1 comprises a hollow axle end 6 directed towards the interior of the housing and a capped nut (not shown in the figure) running in axial alignment with said axle end but propping up from the outer wall of housing 1. Said axle end and capped nut are integrally fitted to the wall of the housing at the level of the longitudinal axis of mouthpiece 2, but in transverse direction to said axis. A first radial axle end hole 7 is located in the walling of said hollow axle end at the end of said mouthpiece 2. The hollow formed inside axle end 6 is in communication with said compressed air duct 5. In addition, there are air inlet holes 8 at the rear wall of said housing 1 opposite said mouthpiece 2, and a curved oblong hole 9 in the side wall of said housing 1.

A cap 10 that can be shifted along guide rails (not shown) on mouthpiece 2 is telescopically connected with an operating lever 11 (FIG. 2) whose free end is pivoted at the above capped nut (not shown). The operating lever 11 also comprises an extension that starts from a pivoted part at its swivelling axis (not shown) , the free end of which is in linkage with an angle lever 23 located in the interior of housing via the curved oblong hole 9 and a tappet 24. The telescopic connection of cap 10 to operating lever 11 hinged to housing 1 allows removal of said cap from mouthpiece 2 while its connection to the inhalation device is retained so that it cannot be lost.

A powder reservoir 12 with a powder discharge hole 12*a* that points towards said axle end 6 is located above said axle end 6 inside said housing 1. There is an inspection glass 13 for level checking at the wall of housing 1 that faces said powder reservoir 12. The powder reservoir 12 consists of a transparent material. A disk 10*a* is fitted to cap 10 to cover the inspection glass 13 for protecting the medicine from sunlight when cap 10 is pushed open.

The interior space of housing 1 is closed towards the opening of mouthpiece 2 by a hinged trip flap 14 that can be swung upwards and outwards. A limit stop 14*a* is mounted to the side of trip flap 14 that points towards the interior of the housing.

The powder discharge hole 12*a* is sealed by dosing ball 15 that tightly fits to its rim and extended rim areas. The dosing ball 15 comprises an axial bore of the bearing 15*a*in which it is pivoted on axle end 6. Furthermore, a torsion spring 16 with a short fixed leg 16*a* and a long movable leg 16*b* rests on axle end 6, said short leg 16*a* being fixed by said dosing ball 15.

The dosing ball 15 comprises a hemispherical dosing cavity 17 at its peripheral surface that points towards said powder reservoir 12 for receiving the powdered form of medication when said cavity is in the range of said powder discharge hole 12*a*.

Said dosing ball 15 further comprises a radial valve hole 18 located in the same sectional level as said first radial axle end hole 7. A blowpipe 19 is connected to the opening of valve hole 18 at the perimeter of dosing ball 15 the open side of which is directed towards said dosing cavity 17. Finally, the peripheral surface of dosing ball 15 comprises a stop piece 20 to arrest said dosing ball 15 either on limit stop 14*a* or at the bottom of housing 1.

A bellows 21 comprising a hole that is connected to the air exit hole 4 is located below said transverse wall 3. At its opposite end, said bellows 21 rests on a support plate 22 that is connected to the above-mentioned angle lever 23 that acts as compression bar. The free end of angle lever 23 that is connected with the extension not shown) of the operating lever 11 outside housing 1 via the oblong hole 9 comprises a protruding rectangular tappet 24 that is in linkage with the long leg 16b of torsion spring 16.

The function of the embodiment described above in static condition of a powder inhalator with compressed air reinforcement shall be described next.

When the powder inhalator is in unused condition, cap 10 is slid onto mouthpiece 2 (FIG. 1) in such a way that intrusion of foreign particles is prevented. It is therefore impossible for a user to remove or lose cap 10 unintentionally or to trigger the administration of the medicine unintentionally when carrying the inhalator in a case, jacket pocket, etc.

The inspection glass 13 is covered by disk 10a and protects the powdered form of medicine in the transparent powder reservoir 12 against sunlight. The trip flap 14 is in its vertical position in which it seals mouthpiece 2. The bellows 21 and torsion spring 16 are in unstressed condition as at the lower position of angle lever 23, and the dosing cavity 17 of the dosing ball rests in the powdered substance, i. e. to the right of the funnel-shaped powder discharge hole 12a as shown in the figure. The powder reservoir 12 is designed to hold a single fill of about 200 doses.

To discharge one dose of the powdered form of medication determined by the size of the dosing cavity 17, the cap 10 is removed from mouthpiece 2 but remains inseparably connected to the operating lever 11 and thus with the device as a whole. When the operating lever 11 is moved downwards, the tappet 24 is swung along the curved oblong hole 9 into its upper position, and the angle lever connected to the operating lever 11 is pressed upwards to compress the bellows 21, thereby compressing the air therein, and to turn the dosing ball 15 with the help of torsion spring 16 first until it its stop piece 20 touches upon limit stop 14a of the trip flap 14 and—from that moment on—to load torsion spring 16 and thus to preload the dosing ball 15. The dosing cavity 17 is located in preloaded condition of the dosing ball 15 at the left edge of powder discharge hole 12a in the figure.

When the user inhales via the mouthpiece 2, the negative pressure that is generated swings the trip flap 14 upwards and releases the dosing ball that is held in place by limit stop 14a, said dosing ball being turned by the force of torsion spring 16 until the stop piece 20 audibly hits onto the bottom of housing 1. At the same time, the radial valve hole 18 in said dosing ball 15 is brought into alignment with the first radial axle end hole 7 of the hollow axle end 6 so that the air compressed in the bellows 21 is impulsively blown via air exit hole 4, compressed air duct 5, the hollow of axle end 6, the radial axle end hole 7, the valve hole 18, and the blowpipe 19 into the dosing cavity 17 which is accurately filled with the powdered medicine and placed outside the range of the powder reservoir 12.

The powdered form of medication is swirled with the stream of the user's inhaled air by the blown in compressed air and the abrupt blocking of the rotation of dosing ball 15 as well as by centrifugal and gravitational forces and carried in fine dispersion into the user's air passages. At the same time, the stream of compressed air boosts the atomization of the powder to guarantee safe inhalation of the powdered medicament even at an inhalation volume below the average value of 1 l/s, e. g. with children and older people. The trip flap 14 falls back into its initial vertical position immediately after inhalation, thus protecting the dosing ball 15 and the powdered substance against moist respiratory air when the patient unintentionally exhales into the mouthpiece 2. Resetting of said trip flap to its initial vertical position is also ensured by a butt that is located in the cap and acts on the trip flap when the cap is closed (not shown).

When the operating lever 11 is moved into the closing position of cap 10, the angle lever 23, the bellows 21 and dosing ball 15 as well as torsion spring 16 are set back to their initial position as shown in FIG. 1, the feed valve for compressed air formed by the axle end hole 7 and the valve hole 18 or the lateral area of the centric bore of the bearing 15a of dosing ball 15 being closed again. A second radial axle end hole 25 also referred to herein as an additional radial axle end hole, is located in the hollow axle end 6 to let air into the bellows 21. When the dosing ball 15 is in its initial position, said second radial axle end hole 25 is in alignment with the valve hole 18 (or another hole not shown here) to allow air to flow into the bellows 21 for another compression process.

The powder inhalator can only be activated again when the cap has been removed and the operating lever been moved again. It is only then that another dose of the medicament can get into the user's respiratory tract, this time carried in the stream of inhaled air only. If the user does not inhale and/or seal the mouthpiece 2 again, the powdered medicament remains in the dosing cavity 17 within the powder reservoir 12. Unintentional double or multiple dosing is excluded. In addition, a noise is produced when the stop piece 20 of the dosing ball 15 hits on the housing bottom and foreign air is blown out of the blowpipe 19 with a hiss, said noise indicating to the user that the powdered medicament really was administered.

Thus the inhalation device can be handled safely and easily even by less skilled users. As its few components are mainly made of injection moulded parts, it can be assembled conveniently and inexpensively in a two-piece housing.

Figure 2:
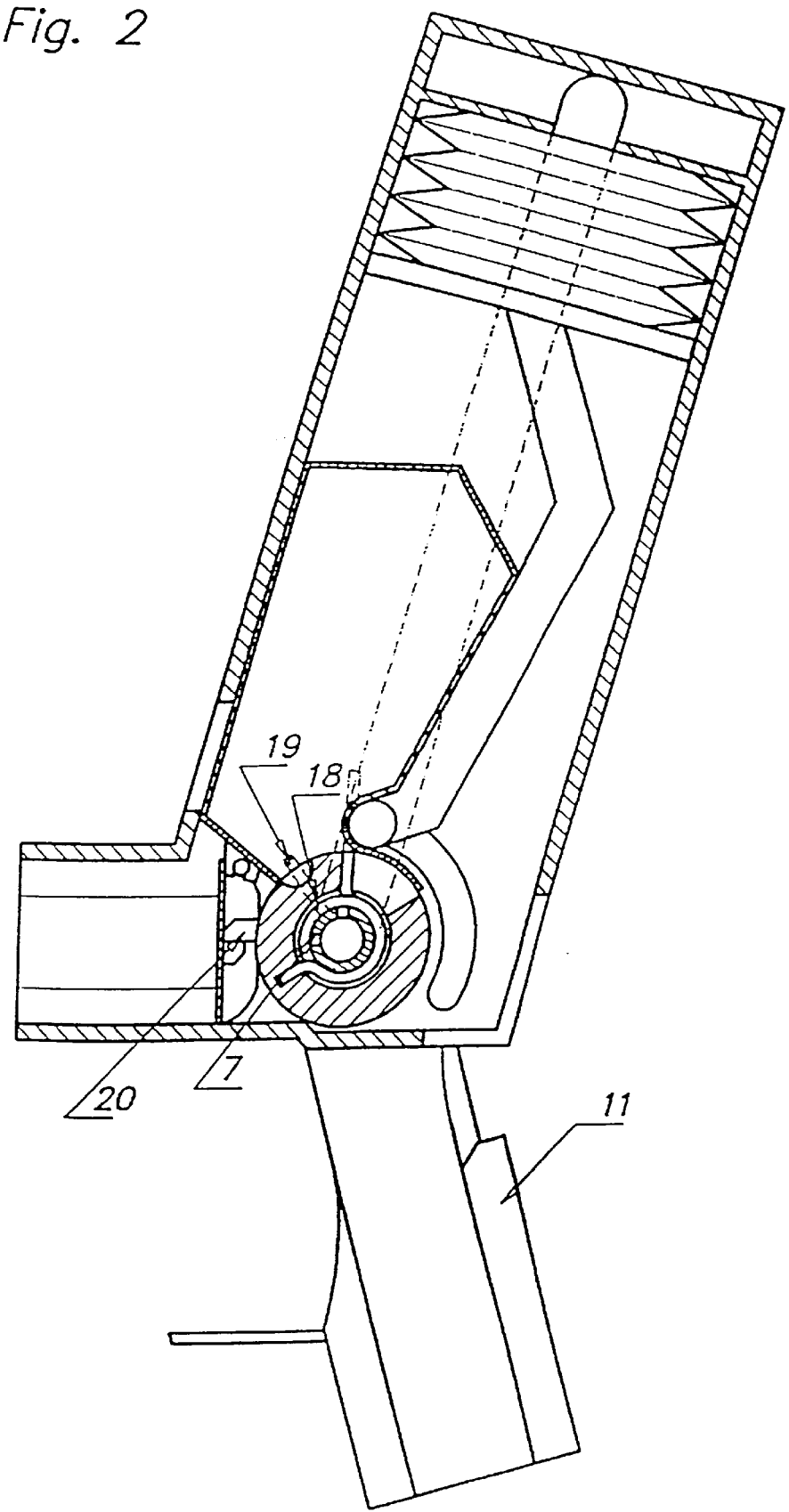
Figure 3:
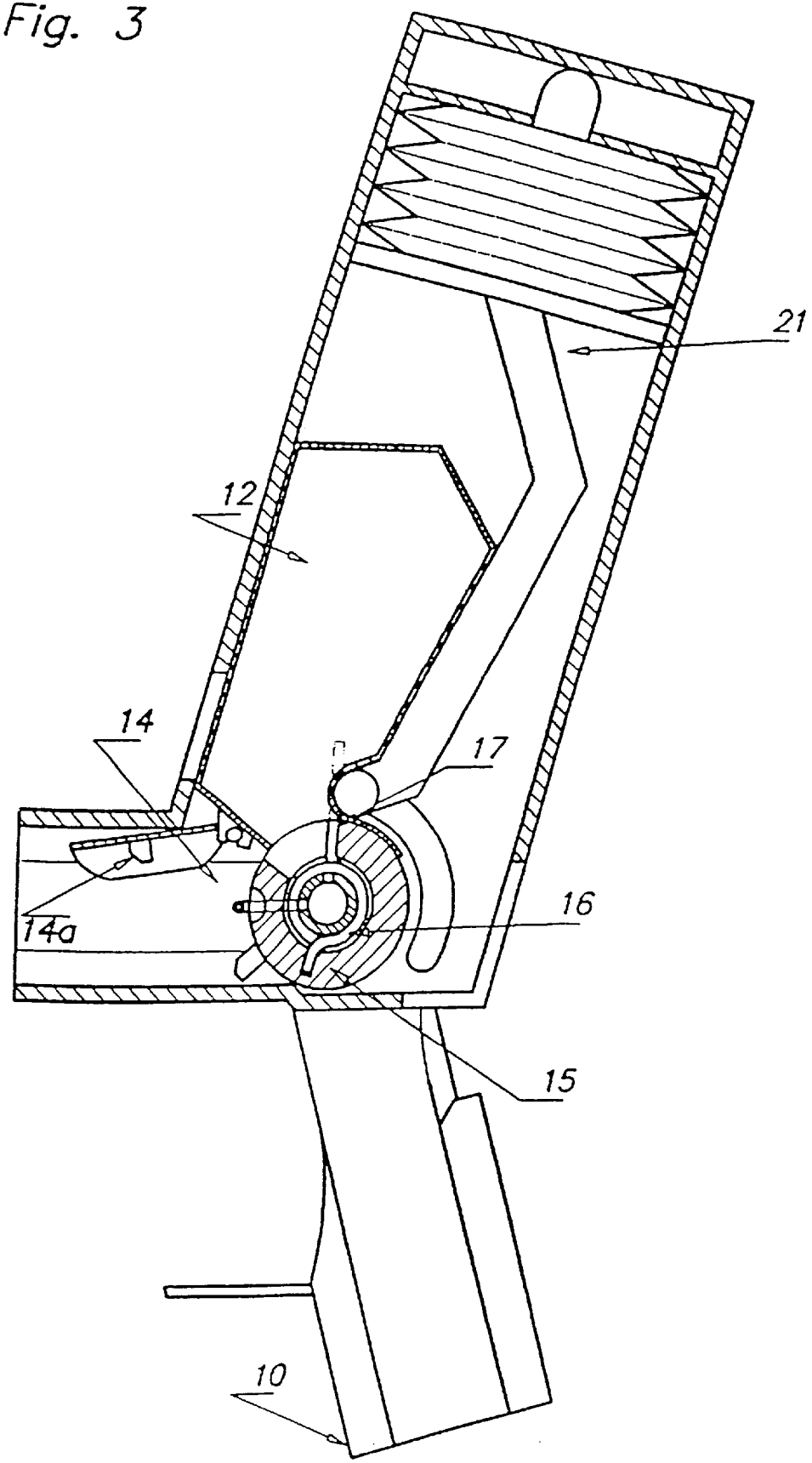
Figure 4:
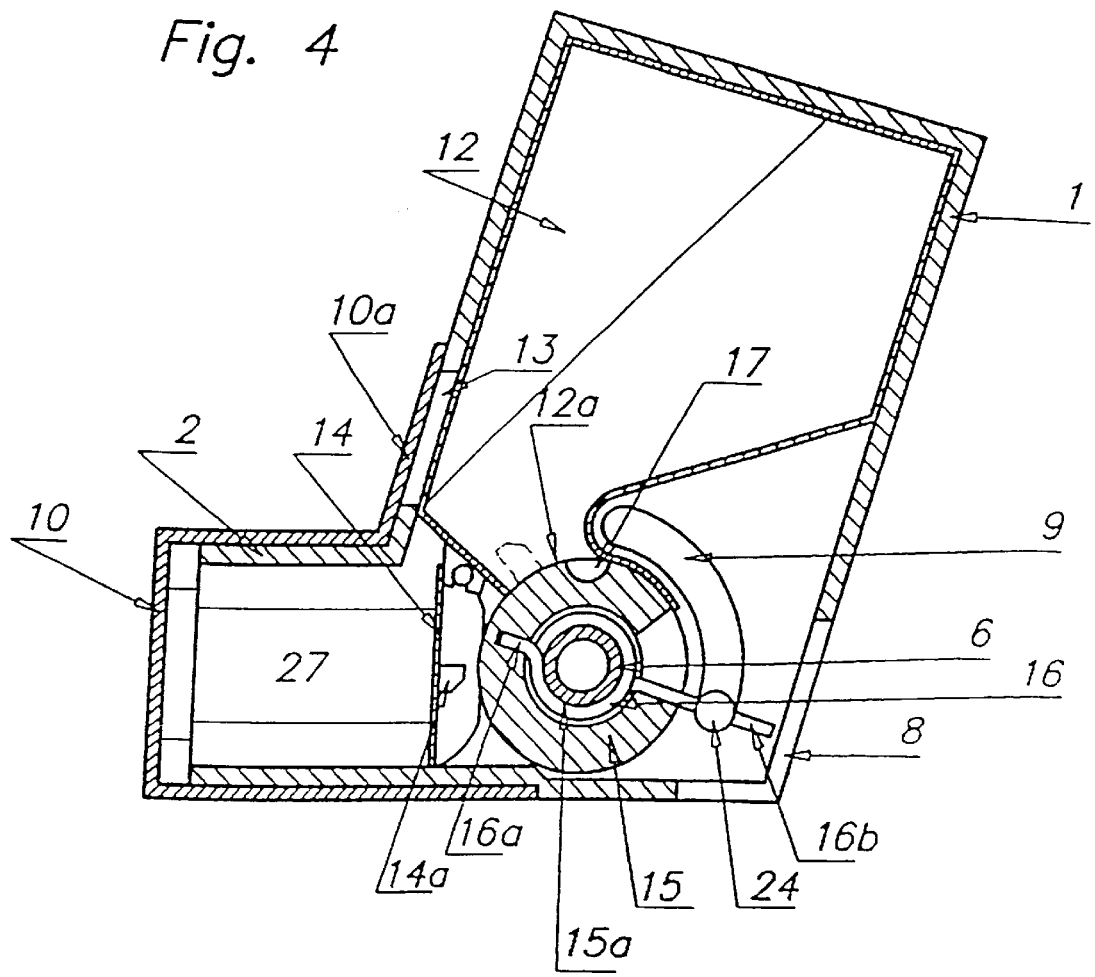

FIG. 4 shows a simplified embodiment of the inhalation device according to the invention, i. e. without the means for generating an additional stream of compressed air. This embodiment is characterized by a simple design and uncomplicated manufacture; it guarantees excellent dispersion of the powdered medicine and reliable intake by the patient even without extra air. The dosing ball 15 is in its relaxed position with the connected torsion spring 16 unloaded in the initial position shown in FIG. 1 when the mouthpiece 2 is sealed by cap 10. The tappet 24 of the operating lever 11 that is linked to the long leg 16b of the torsion spring 16 is at its lower position in oblong hole 9. When the cap 10 is removed from the mouthpiece 2 and the operating lever 11 moved to the position shown in FIG. 2, the dosing ball 15 turns simultaneously with the motion of the tappet 24 until the stop piece 20 of said dosing ball 15 hits on limit stop 14a. When the operating lever 11 is moved on until its tappet 24 hits on the other, upper end of the oblong hole 9, the torsion spring 16 is bent, and the dosing ball 15 whose dosing cavity 17 is placed immediately at the rim of the powder reservoir 12 is preloaded. When the patient inhales and the negative pressure thereby generated in the mouthpiece results in flinging up the trip flap 14, the dosing ball is suddenly released. Its accelerated movement due to preloading is abruptly blocked when the stop piece 20 hits on the bottom of mouthpiece 2.

Sudden acceleration and blocking of the motion of the powdered form of medication contained in the dosing cavity 17 and centrifugal forces result in complete detachment of the medicine from the dosing cavity 17 and its dispersion and swirling across a large area in their duct of the mouthpiece 2. Complete intake of the powder dose by the patient is guaranteed without an additional stream of compressed air by simultaneous and, due to the negative pressure, intermittent feed of inhalation air.

Figure 5:
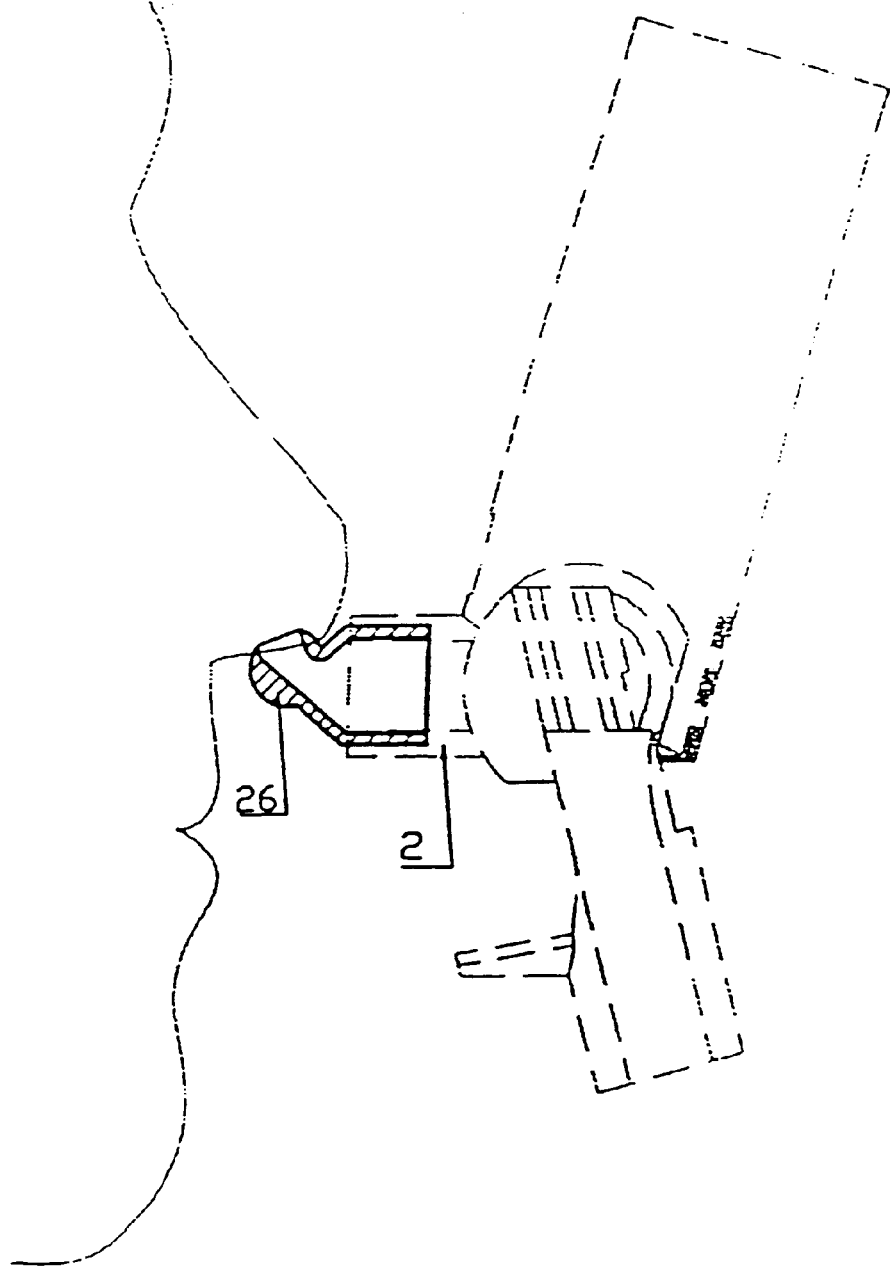

FIG. 5 shows an embodiment of said powder inhalator with an integrated monorhinal adapter 26 inserted into the mouthpiece 2. Said nasal adapter 26 can be mounted fixedly or detachably or may be inseparably inserted into the mouthpiece at a later point in time. Said nasal adapter 26 has a unique design to fit to a specific inhalation device only.

FIG. 6 shows the inhalation device with its cap 10 completely slid onto the mouthpiece 2, with its cap 10 removed from the mouthpiece 2, and with its cap 10 removed and the operating lever 11 that activates the inhalator moved downwards. FIG. 5 clearly shows that the cap 10 is guided on a rail profile 11a along said operating lever; it extends the operating lever telescopically but always stays connected to it.

All powdered forms of medication can be administered using the inhalation device according to the invention. It has proved to be particularly advantageous for treating asthmatic diseases and the like.

Active ingredients to be administered can be, for example, beta-sympathomimetics and corticoids. It is particularly suited for the following substances and combinations/mixtures thereof: salbutamol, cromolyn sodium, budesonide, beclometason, reproterol, fenoterol.

| | |
|---|---|
| 1 | housing |
| 2 | mouthpiece |
| 3 | transverse wall |
| 4 | air exit hole |
| 5 | compressed air duct |
| 6 | hollow axle end |
| 7 | first radial axle end hole (air outlet) |
| 8 | air inlet holes |
| 9 | curved oblong hole |
| 10 | cap |
| 10a | disk |
| 11 | operating lever |
| 11a | rail profile |
| 12 | powder reservoir |
| 12a | powder discharge hole |
| 13 | inspection glass |
| 14 | trip flap |
| 14a | limit stop |
| 15 | dosing ball |
| 15a | bore of bearing |
| 16 | torsion spring |
| 16a | short leg of 16 |
| 16b | long leg of 16 |
| 17 | dosing cavity |
| 18 | valve hole in 15 |
| 19 | blowpipe |
| 20 | stop piece of 15 |
| 21 | bellows |
| 22 | support plate |
| 23 | angle lever |
| 24 | tappet |
| 25 | second radial axle end hole (air inlet) |
| 26 | nasal adapter |
| 27 | air duct |

What is claimed is:

1. An inhalation device for powdered forms of medication, comprising:
    a housing with a rotatable dosing apparatus that has a circular perimeter and is associated with a powder discharge hole of a powder reservoir located inside the housing, wherein the dosing apparatus is manually operable and includes a peripheral dosing cavity for receiving a dose of powder; and
    a mouthpiece connected to the housing at the level of the dosing apparatus and opposite from air intake holes defined in the housing so as to form an air duct in which a powder dose released by turning the dosing apparatus is catapulted into a user's stream of respiratory air,
    wherein the dosing apparatus is connected with elastic fastening devices and includes a stop piece,
    wherein the dosing apparatus can be preloaded until it hits on a movable limit stop while the dosing cavity of the dosing apparatus remains within the range of the powder discharge hole of the powder reservoir located within the housing,
    wherein the limit stop is movable by the user's breathing air for releasing the preloaded dosing apparatus, and
    wherein accelerated motion of the dosing apparatus may be blocked suddenly by the stop piece.

2. The inhalation device according to claim 1, wherein the dosing apparatus is a dosing ball that includes a bearing with a centric bore, and wherein the dosing ball is pivotable around an axle end of the housing.

3. The inhalation device according to claim 2, wherein the elastic fastening device is a torsion spring pivotable on the axle end of the housing and having a short leg and a long leg, the short leg connected with the dosing ball, and the long leg connected with a pivotable operating lever of the device at an outer side of an exterior of the housing via a curved oblong hole defined in the housing and in axial alignment with the axle end of the housing for turning and preloading the dosing ball.

4. The inhalation device according to claim 3, wherein the operating lever is guided using a tappet in the oblong hole and is configured to be arrested with the dosing ball in preloaded position by one of interlocking and passing over a dead centre.

5. The inhalation device according to claim 3, wherein a cap is slidably mounted to a free end of the operating lever, and wherein the cap is slidable onto the mouthpiece when the operating level is in an initial position.

6. The inhalation device according to claim 5, wherein a disk is fitted to the cap, and wherein the cap covers an inspection glass provided in the housing adjacent a lower part of the powder reservoir when the cap is slid onto the mouthpiece.

7. The inhalation device according to claim 2, wherein the dosing ball is removable from the housing.

8. The inhalation device according to claim 1, wherein the dosing apparatus is a dosing ball, wherein the limit stop is movable in sync with the user's respiration and is mounted to a trip flap that seals the air duct,
    wherein the limit stop is pivotable in the housing directly in front of the dosing ball and in linkage with the stop piece of the dosing ball when the dosing ball is in preloaded position, the dosing ball positioned in the air, duct such that the stop piece contacts the bottom of the housing by action of a torsion spring after the movable trip flap is released, and
    wherein the dosing cavity is placed outside the range of the powder discharge hole.

9. The inhalation device according to claim 1, wherein the powder reservoir is made of a transparent material, and wherein an inspection glass is provided in the housing adjacent a lower part of the powder reservoir.

10. The inhalation device according to claim 1, wherein the dosing cavity is a recess having a hemispherical shape.

11. The inhalation device according to claim 1, wherein a nasal adapter for intranasal inhalation is one of detachably and fixedly inserted into the mouthpiece.

12. The inhalation device according to claim 11, wherein the nasal adapter comprises a component protruding from an opening of the mouthpiece, and wherein the component includes a flow duct that is sealed airtight when put against a nostril of the user.

13. The inhalation device according to claim 1, wherein the powder reservoir is configured to hold a single fill of about 200 doses of powdered active medicinal substance.

14. The inhalation device according to claim 1, wherein the dosing apparatus is a dosing ball, and wherein a pumping device is provided inside the housing, the pumping device including a compressed air reservoir which is in fluid communication with the dosing cavity via a valve such that compressed stored in the compressed air reservoir is released by the valve simultaneously with the release of the dosing ball by the movable limit stop.

15. The inhalation device according to claim 14, wherein the pumping device is connected at one end with a bellows held on a movable support plate, wherein an opposite end of the pumping device is supported against a transverse wall in the housing via an angle lever, wherein the angle lever is a means of power transmission, wherein the angle lever is connected at an opposite end thereof to a tappet of an operating lever of the device, and wherein the bellows is in communication with a hollow space in an axle end of the housing via an air exit hole to a compressed air duct in the housing and a radial axle end hole defined in the housing.

16. The inhalation device according to claim 15, wherein the dosing ball includes a bearing with a centric bore, and where in the valve for controlling the compressed air in sync with respiration from the bellows to the air duct is formed by the radial axle end hole, an additional radial axle end hole defined in the housing, a wall of the bore of the bearing of the dosing ball, and a radial valve hole in the dosing ball, the radial valve hole in alignment with one of the radial axle end holes when the stop piece rests on the bottom of the housing.

17. The inhalation device according to claim 16, wherein a curved blowpipe is connected to the radial valve hole in a peripheral surface area of the dosing ball, and wherein an opening of the blowpipe points from outside the dosing ball towards the dosing cavity.

* * * * *

UNITED STATES PATENT AND TRADEMARK OFFICE
CERTIFICATE OF CORRECTION

PATENT NO.   : 6,752,147 B1
DATED        : June 22, 2004
INVENTOR(S)  : Goldemann et al.

It is certified that error appears in the above-identified patent and that said Letters Patent is hereby corrected as shown below:

Title page,
Item [54], Title, should read:  -- INHALATION DEVICE FOR ADMINISTERING POWDERED FORMS OF MEDICATION --

Item [57], ABSTRACT, should read:

-- An inhalation device includes a housing with a rotatable dosing ball associated with an opening of a powdered reservoir located inside the housing. The dosing ball may be operated manually and includes a peripheral dosing cavity for receiving a dose of powder. The dosing ball is connected to a torsion spring and further includes a stop piece. The dosing ball is associated with a pivotable trip flap that has a movable limit and is preloaded by turning the dosing ball until the stop piece comes to rest on the movable limit stop of the trip flap. The dosing ball is released, and the stop piece contacts the bottom of the housing which blocks acceleration of the dosing ball causing the medicine to be dispersed in the stream of respiratory air.  --

Column 7,
Line 66, "includes a perpheral" should read -- includes a peripheral --

Column 8,
Lines 53-54, "air, duct" should read -- air duct, --

Signed and Sealed this

Twenty-third Day of November, 2004

JON W. DUDAS
*Director of the United States Patent and Trademark Office*